United States Patent [19]

Wolleb

[11] Patent Number: 5,663,326

[45] Date of Patent: Sep. 2, 1997

[54] MIXTURES OF ISOMERIC SUBSTITUTED PHTHALOCYANINES, AND PROCESS FOR THEIR PREPARATION

[75] Inventor: Heinz Wolleb, Marly, Switzerland

[73] Assignee: Ciba-Geigy Corporation, Tarrytown, N.Y.

[21] Appl. No.: 529,822

[22] Filed: Sep. 18, 1995

[30] Foreign Application Priority Data

Sep. 23, 1994 [CH] Switzerland .................. 2906/94

[51] Int. Cl.$^6$ .................. C09B 47/18; C09B 67/12
[52] U.S. Cl. .................. 540/139; 540/122; 540/140
[58] Field of Search .................. 540/122, 128, 540/139, 140, 129

[56] References Cited

U.S. PATENT DOCUMENTS

| H477 | 6/1988 | Barger et al. .................. 540/140 |
| 5,280,114 | 1/1994 | Itoh et al. .................. 540/128 |

FOREIGN PATENT DOCUMENTS

| 0337209 | 10/1989 | European Pat. Off. . |
| 0373643 | 6/1990 | European Pat. Off. . |
| 0492508 | 7/1992 | European Pat. Off. . |
| 0513370 | 11/1992 | European Pat. Off. . |
| 0519419A2 | 12/1992 | European Pat. Off. . |

OTHER PUBLICATIONS

Derwent Abstract 89–314182/43 of JP–A–01/233,401 1989.

Derwent Abstract 93–021894/03 of JP–A–04/348,168 1993.

M. Emmelius et al., Angewandte Chemie 1989/11, pp. 1475–1502.

Nouveau Journal De Chimie, vol. 6, pp. 653–658 (1982).

Itoh et al. C.A. 118 : 214980., 1993 Amorphous phthalocanines or their mixtures.

*Primary Examiner*—John M. Ford
*Assistant Examiner*—Pavanaram K. Sripada
*Attorney, Agent, or Firm*—Michele Kovaleski; Kevin T. Mansfield

[57] ABSTRACT

Mixtures of four α-alkoxy-substituted phthalocyanine isomers, predominantly

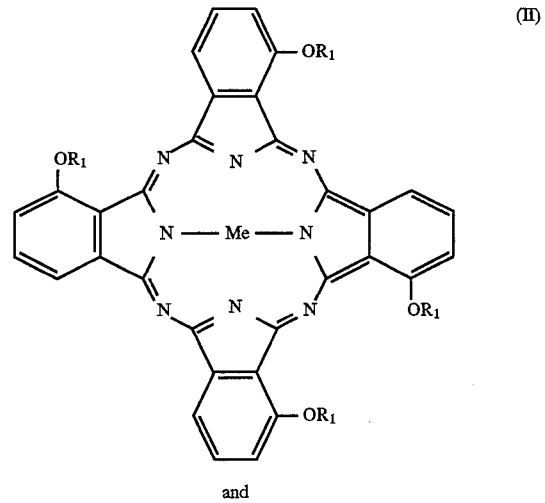

and

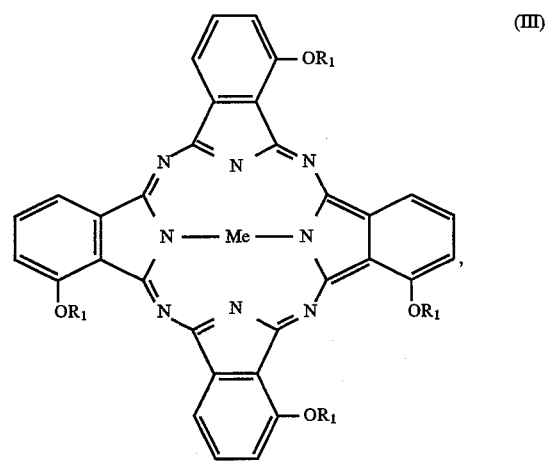

or of four β-alkoxy-substituted phthalocyanine isomers, where Me is a divalent metal atom or a divalent oxo metal, $R_1$ is a linear or branched $C_1$–$C_{16}$alkyl, $C_3$–$C_{16}$alkenyl or $C_3$–$C_{16}$alkynyl radical which is unsubstituted or substituted by $C_1$–$C_{12}$alkoxy, —CN, $NO_2$, halogen, —OH, phenyl, cyanophenyl, nitrophenyl, halophenyl, hydroxyphenyl or ($C_1$–$C_{12}$alkoxy)phenyl, wherein two isomers of the formula II and of the formula III make up at least 80% of the total mixture and the two other isomers make up at most 20% of the total mixture, with the ratio between the compounds of the formula II and the compounds of the formula III being from 0.3 to 3.0:1.

The isomer mixtures can be obtained by reacting α- or β-alkoxyphthalodinitriles in the presence of a metal salt, a Lewis acid, a nitroaromatic compound as solvent and at least equimolar amounts of urea, based on the phthalodinitrile.

12 Claims, No Drawings

MIXTURES OF ISOMERIC SUBSTITUTED PHTHALOCYANINES, AND PROCESS FOR THEIR PREPARATION

The invention relates to a mixture of isomeric alkoxy-substituted phthalocyanines and to a process for their preparation by reacting compounds of the formula V

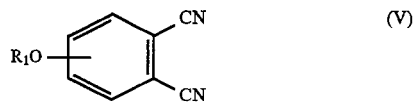

in the presence of a metal salt, a Lewis acid, urea and selected solvents.

The use of dyes which absorb radiation in the near infra-red (NIR) region for recording information in WORM (write once read many) systems has been known for some time and is described, for example, by M. Emmelius et al. in Angewandte Chemie, Issue 11, pages 1475–1502 (1989). The change in absorption which is necessary for recording information in the form of bits can be achieved by physical changes (for example by sublimation or diffusion) or by chemical changes (for example photochromicity, isomerization or thermal decomposition) by laser irradiation in such recording materials.

Substituted phthalocyanines are an important class of dyes for use in such WORM systems, since they can have a high NIR absorption in the region from 700 to 900 nm if they have appropriate peripheral substitution, depending on the central metal atom. In addition to the absorption properties, their solubility in organic solvents, especially aliphatic hydrocarbons, is of great importance, since the absorption layer of optical storage materials is frequently produced in a spin-coating process from an organic solvent.

EP-A-337 209 describes polysubstituted alkylphthalocyanines which can be obtained by reacting substituted phthalodinitriles in high-boiling solvents in the presence of a Lewis acid. The solvents proposed are urea, chloronaphthalene, nitrobenzene, alcohols and amino alcohols. The reaction temperature can be, for example, 250° C. The solubility of the resultant alkylphthalocyanines in organic solvents and the composition of the reaction product are not described.

The preparation of alkoxy-substituted phthalocyanines is likewise known, and the isomeric tetraisoprepoxyphthalocyanines are described in Nouveau Journal de Chemie, Vol. 6, pp. 653–658 (1982). The reaction is carded out, for example, on polymer-bonded phthalodinitdle and gives a pure isomer. If the reaction is carded out at elevated temperature in dimethylaminoethanol without polymer bonding, an isomer mixture of unknown distribution is formed.

Another process for the preparation of α-alkoxy-substituted phthalocyanines is described, for example, in EP-A-0 373 643 and EP-A-0 492 508. EP-A-0 373 643 describes the formation of a single symmetrical isomer on heating a mixture of α-alkoxyphthalodinitfile, metal salt, base and alcohol to reflux. In EP-A-0 492 508, by contrast, α-alkoxyphthalodinitrile and an organic base are heated in an alcohol to 90°–120° C. and a metal salt is added at this temperature, giving, as main products, 2 positional isomers in a ratio of from 40:60 to 60:40, of which one is readily soluble and the other less soluble in organic solvents. An alternative given in EP-A-0 492 508 is to use the corresponding diiminoisoindoline. By varying the addition of base and the temperature, the isomer ratio can be modified. In each case 2 isomers are formed, of which the more highly soluble is in an excess of from 85–95 parts to 5–15 parts. This process variant has the disadvantage that the diiminoisoindoline must be prepared first, meaning that a further reaction step is necessary. Furthermore, both the variants described in EP-A-0 492 508 give predominantly only two of the 4 possible isomers, and only one of the two more highly soluble, which has an adverse effect on the association and crystallization behaviour.

In general, a mixture of a plurality of readily soluble isomers has a lower tendency toward association and crystallization than one in which a single isomer predominates or in which significant amounts (for example ≧10%) of low-solubility isomers are present.

The present invention relates to a readily soluble isomer mixture predominantly comprising two readily soluble positional isomers of alkoxy-substituted phthalocyanines, and to a process in which a) good yields are obtained and b) asymmetrical positional isomers are formed preferentially, thus achieving good solubility of the α- or β-alkoxy-substituted phthalocyanines in organic solvents. The isomer mixtures can also serve as intermediates for further reactions. Thus, for example, as described in EP-A-0 513 370, they can be reacted with halogen to give the corresponding halogenated alkoxyphthalocyanines, where a multiplicity of isomers can be formed, which is advantageous for the solubility and shelf life of the solution. In these halogenated isomer mixtures of phthalocyanines, halogen can furthermore be replaced by at least one phosphorus substituent, which allows the polarity of the compounds and thus their solubility to be matched to a wide variety of solvents.

The invention relates to a mixture of isomeric α-alkoxy-substituted phthalocyanines of the formulae I–IV

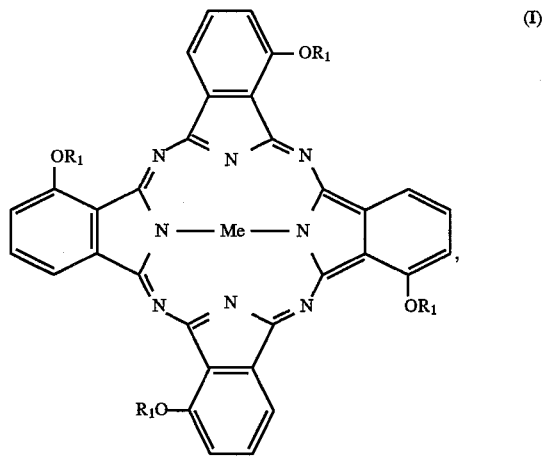

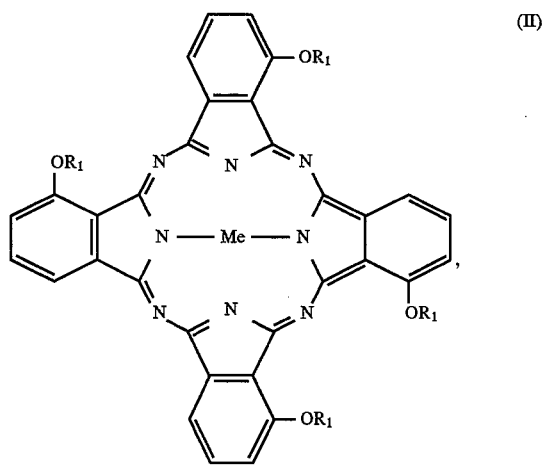

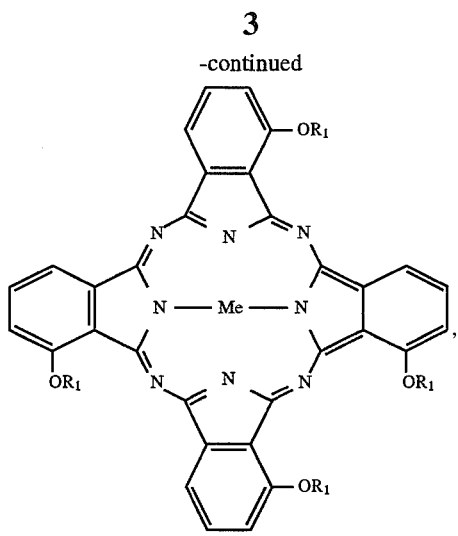
(III)
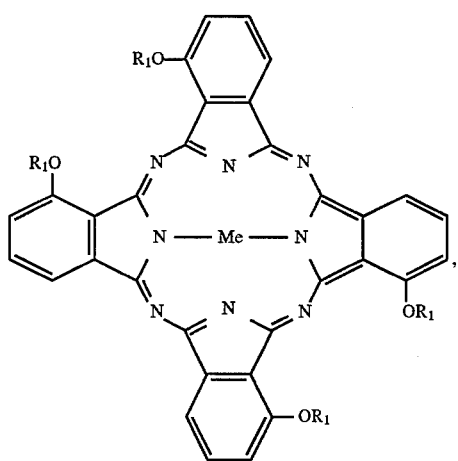
(IV)
or β-alkoxy-substituted phthalocyanines of the formulae Ia–IVa
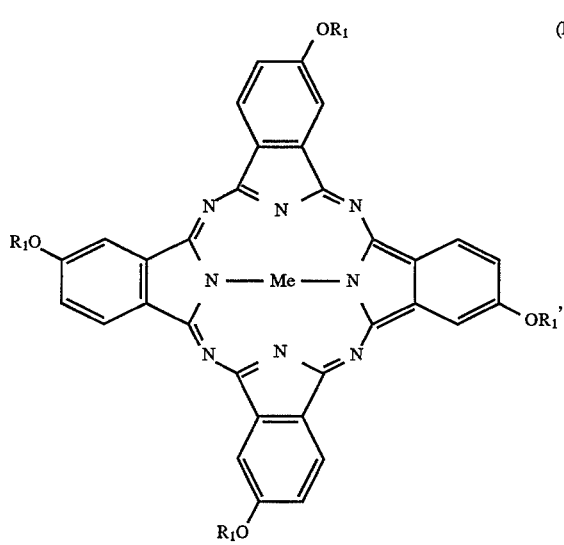
(Ia)
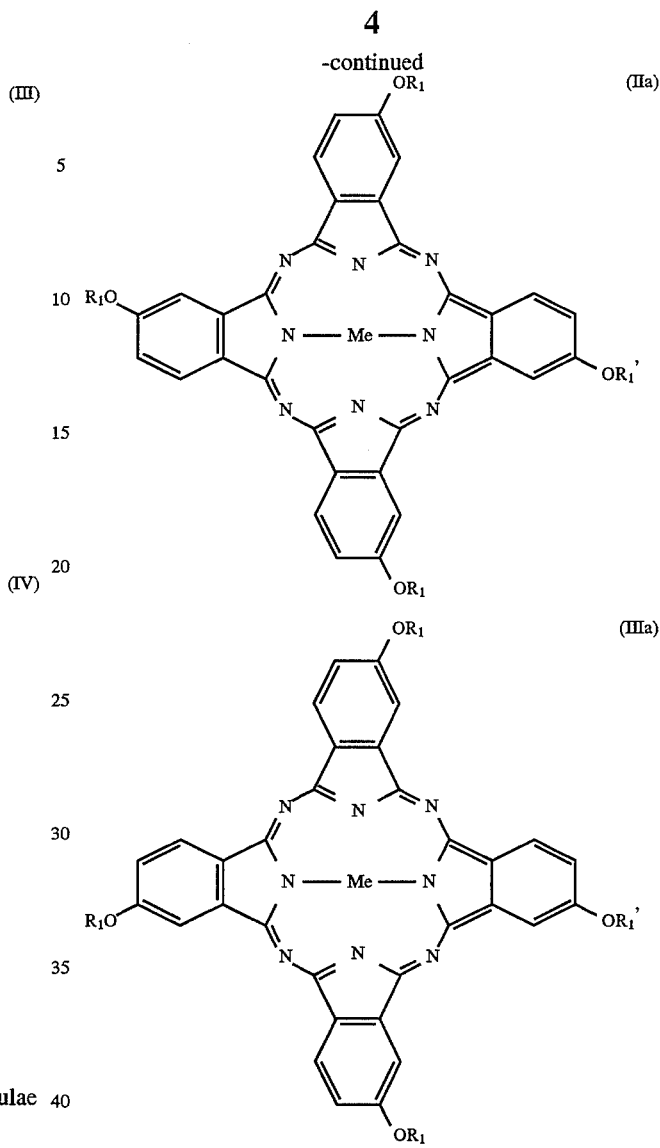
(IIa)
(IIIa)
(IVa)
where
Me is a divalent metal atom or a divalent oxo metal,
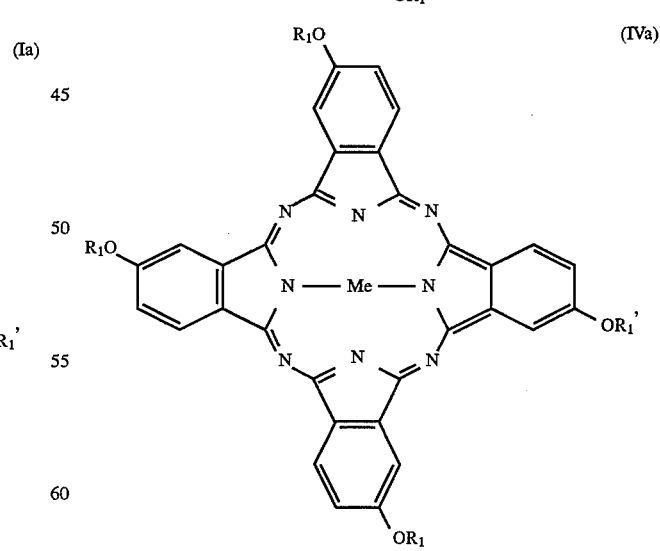

$R_1$ is a linear or branched $C_1$–$C_{16}$alkyl, $C_3$–$C_{16}$alkenyl or $C_3$–$C_{16}$alkynyl radical, which is unsubstituted or substituted by $C_1$–$C_{12}$alkoxy, —CN, $NO_2$, halogen, —OH, phenyl, cyanophenyl, nitrophenyl, halophenyl, hydroxyphenyl or ($C_1$–$C_{12}$alkoxy)phenyl, wherein the isomers of the formula II or IIa and of the formula III or IIIa make up at least 80% of the total mixture, and the isomers of the formula I or Ia and of the formula IV or IVa make up at most 20% of the total mixture, with the ratio between the compounds of the formula II or IIa and the compounds of the formula III or IIIa being from 0.3 to 3.0:1.

For the purposes of the present invention, percentage data are % by weight.

Preference is given to isomer mixtures in which the isomers of the formula II or IIa and of the formula III or IIIa make up at least 90% of the total mixture, and the isomers of the formula I or Ia and of the formula IV or IVa make up at most 10% of the total mixture.

Particular preference is given to isomer mixtures in which the isomers of the formula II or IIa and of the formula III or IIIa make up at least 95% of the total mixture, and the isomers of the formula I or Ia and of the formula IV or IVa make up at most 5% of the total mixture.

In particular, preference is given to isomer mixtures in which the ratio between the compounds of the formula II or IIa and the compounds of the formula III or IIa is from 0.5 to 2.0:1.

Examples of linear or branched $C_1$–$C_{16}$alkyl radicals are methyl, ethyl and the various positional isomers of propyl, butyl, pentyl, hexyl, heptyl, octyl, nonyl, decyl, undecyl, dodecyl, tridecyl, tetradecyl, pentadecyl and hexadecyl.

Preference is given to $C_4$–$C_{12}$alkyl radicals.

Examples of $C_3$–$C_{16}$alkenyl radicals are propenyl, butenyl, pentenyl, hexenyl, heptenyl, octenyl, nonenyl, decenyl, undecenyl, dodecenyl, tridecenyl, tetradecenyl, pentadecenyl and hexadecenyl with their various positional isomers.

Preference is given to $C_4$–$C_2$alkenyl radicals.

Examples of $C_3$–$C_{16}$alkynyl radicals are propynyl, butynyl, pentynyl, hexynyl, heptynyl, octynyl, nonynyl, decynyl, undecynyl, dodecynyl, tridecynyl, tetradecynyl, pentadecynyl and hexadecynyl with their various positional isomers.

Preference is given to $C_4$–$C_{12}$alkynyl radicals.

The alkyl, alkenyl and alkynyl radicals are preferably branched.

Halogen is, for example, fluorine, bromine, chlorine or iodine.

Examples of $C_1$–$C_{12}$alkoxy radicals are methoxy, ethoxy and the various positional isomers of propoxy, butoxy, pentoxy, hexyloxy, heptyloxy, octyloxy, nonyloxy, decyloxy, undecyloxy and dodecyloxy.

Preference is given to $C_1$–$C_8$alkoxy.

Suitable divalent metal atoms or oxo metals are a multiplicity of metals, as described, for example, by F. H. Moser, A. L. Thomas, in The Phthalocyanines, CRC Press 1983.

The divalent metal atom or oxo metal is preferably Cu(II), Zn(II), Fe(II), Ni(II), Ru(II), Rh(II), Pd(II), Pt(II), Mn(II), Mg(II), Be(II), Ca(II), Sa(II), Cd(II), Hg(II), Sn(II), Co(II), Pb(II) or VO, MnO, TiO.

Particular preference is given to the divalent metal atoms Zn(II), Sn(II), Cu(II), Ni(II), Co(II), Pb(II) or Pd(II).

Very particular preference is given to the divalent metal atoms Pd(II), Cu(II) or Ni(II), in particular Cu(II) and especially Pd(II).

In a preferred sub-group, $R_1$ is a linear or branched $C_1$–$C_{16}$alkyl radical which is unsubstituted or substituted by $C_1$–$C_{12}$alkoxy, —CN, $NO_2$, halogen, —OH, phenyl, cyanophenyl, nitrophenyl, halophenyl, hydroxyphenyl or ($C_1$–$C_{12}$alkoxy)phenyl.

In a particularly preferred sub-group, $R_1$ is a linear or branched $C_4$–$C_{12}$alkyl radical which is unsubstituted or substituted by $C_1$–$C_{12}$alkoxy, —CN, $NO_2$, halogen, —OH, phenyl, cyanophenyl, nitrophenyl, halophenyl, hydroxyphenyl or ($C_1$–$C_{12}$alkoxy)phenyl.

$R_1$ is very particularly preferably an unsubstituted linear or branched $C_4$–$C_{12}$alkyl radical, in particular a branched $C_4$–$C_{12}$alkyl radical, for example 2,4-dimethyl-3-pentoxy.

The substitution can take place either in the β-position or in the α-position, but the —$OR_1$ substituent is preferably in the α-position.

In the case of α-substitution, the 4 positional isomers of the formulae I to IV can form during the reaction. Preference is given to isomer mixtures of compounds of the formulae I to IV.

The individual positional isomers differ through their solubility in organic solvents, in particular in aliphatic hydrocarbons. The highly symmetrical isomers of the formulae I and IV have the lowest solubility.

In the case of β-substitution, the corresponding 4 isomers of the formulae Ia to IVa can arise; within this series, the isomers of the formulae Ia and IVa likewise have the lowest solubilities.

The invention furthermore relates to a process for the preparation of a mixture of isomeric compounds of the formulae I to IV or Ia to IVa in which the isomers of the formula II or IIa and of the formula III or IIIa make up at least 80% of the total mixture and the isomers of the formula I or Ia and of the formula IV or IVa make up at most 20% of the total mixture, and the ratio between the compounds of the formula II or IIa and the compounds of the formula III or IIIa is from 0.3 to 3.0:1, by reacting compounds of the formula V

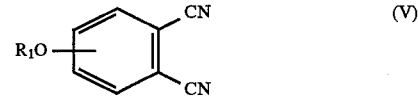

(V)

in the presence of a metal salt and a Lewis acid, where $R_1$ is as defined above, which comprises carrying out the reaction in the presence of nitrobenzene, nitrotoluene or nitroxylene and an at least equimolar amount of urea, based on the compounds of the formula V.

Preference is given to metal salts in which the anion is derived from a monobasic or dibasic inorganic acid, a $C_1$–$C_{12}$carboxylic acid or a $C_5$–$C_{12}$-β-diketone.

Suitable inorganic acids are in particular HCl, HBr, $H_2SO_4$, $HNO_3$ and $HClO_4$. Examples of suitable $C_1$–$C_{12}$carboxylic acids are formic acid, acetic acid, propionic acid, the various isomers of butyric acid, valeric acid and caproic acid. Examples of suitable $C_5$–$C_{12}$-β-diketones are acetylacetone, hexane-2,4-dione, heptane-3,5-dione, heptane-2,4-dione, and the various positional isomers of octane-, nonane-, decane-, undecane- and dodecane-β-diones.

The metal salt is particularly preferably Pd(II)$Cl_2$, Cu(II)$Cl_2$, Zn(II)$Cl_2$, Ni(II)$Cl_2$, Cu(II) acetylacetonate or V(III) acetylacetonate.

Very particular preference is given to Pd(II)$Cl_2$, Cu(II)$Cl_2$ and Ni(II)$Cl_2$.

The reaction is preferably carried out at a molar ratio between the compounds of the formula V and urea of from 1:1 to 1:20, particularly preferably in a molar ratio of from 1:1 to 1:10.

The weight ratio between urea and nitrobenzene, nitrotoluene or nitroxylene is preferably from 1:1 to 1:50, particularly preferably from 1:5 to 1:20.

The process is preferably carried out at a temperature of from 130° to 250° C., particularly preferably at a temperature of from 130° to 190° C.

The pressure conditions are not crucial per se, but the process is preferably carried out at a pressure of from $1 \cdot 10^5$ to $20 \cdot 10^5$ Pa.

The reaction time may differ depending on the metal atom; it is preferably from 0.5 to 24 hours.

A large number of Lewis acids are known to the person skilled in the art, for example $AlCl_3$, $AlBr_3$, $BF_3$, $BCl_3$, $SbCl_3$, $SbBr_3$, $AsBr_3$, $AsCl_3$, $ZnCl_2$, $ZnBr_2$, $SnCl_2$, $SnBr_2$, ammonium molybdate and ammonium molybdate tetrahydrate, and others.

The Lewis acid is preferably ammonium molybdate or ammonium molybdate tetrahydrate.

The Lewis acid is preferably employed in an amount of from 0.1 to 5% by weight, based on the compounds of the formula Y.

The invention also relates to a material for the optical recording and storage of information in which a layer of a phthalocyanine of the formula I–IV or of the formula Ia–IVa prepared in accordance with the invention has been applied as recording material to a transparent, dielectric carrier. A reflection layer and protective coating may additionally have been applied to the material. The embodiments described in EP-A-0 546 994, for example, also apply.

The novel information-containing material represents, in particular, an optical information material of the WORM type. It can be used, for example, as a playable compact disc (CD), as a storage material for computers or as an identity and security card.

The invention therefore furthermore relates to the use of the isomer mixtures of claim 1 in optical storage media for information recording in WORM systems.

The examples below illustrate the invention.

EXAMPLE 1

50 g (206 mmol) of 3-(2,4-dimethyl-3-pentoxy) phthalodinitrile, 9.1 g (51.7 mmol) of anhydrous palladium chloride, 24.8 g (413 mmol) of urea and 1 g (2% by weight) of ammonium molybdate are introduced into 200 ml of nitrobenzene, and the mixture is heated to 160° C. with stirring under an argon atmosphere. The mixture is subsequently stirred at this temperature for 4 hours, then cooled to RT, diluted with toluene and filtered through a filter aid. The filtrate is evaporated to dryness at 100° C./$10^{-1}$ mbar. The residue is taken up in 400 ml of toluene, and filtered through 500 g of silica gel using toluene as eluent. The toluene phase is evaporated to 250 ml and subsequently added dropwise to 1.5 l of methanol. The precipitate is filtered off and washed twice with 100 ml of methanol, then dried at 60° C./165 mbar for 12 hours, giving 35.2 g (59% of theory) of a greenish-blue solid having a $\lambda_{max}$ of 702 nm ($\epsilon$=215 190 $l \cdot mol^{-1} \cdot cm^{-1}$) in N-methylpyrrolidone (NMP). The NMR shows that the isomers I, II and III are present in a ratio of 5:53:42.

EXAMPLE 2

5.0 g (20.6 mmol) of 3-(2,4-dimethyl-3-pentoxy) phthalodinitrile, 1.35 g (5.15 mmol) of copper acetylacetonate, 2.5 g (41.3 mmol) of urea and 0.1 g (2% by weight) of ammonium molybdate are introduced into 20 ml of nitrobenzene, and the mixture is heated to 160° C. with stirring under an argon atmosphere and subsequently stirred at this temperature for 4 hours. The mixture is subsequently cooled to RT, diluted with toluene and filtered through a filter aid. The filtrate is evaporated to dryness at 100° C./$10^{-1}$ mbar. The residue is taken up in methylene chloride, 100 g of silica gel are added, the solvent is evaporated, the mixture is then transferred onto a glass suction filter, and the product is eluted with hexanelethyl acetate 25:1. The filtrate is evaporated, the residue is dissolved in 30 ml of toluene, and the solution is added dropwise to 400 ml of methanol. The precipitate is filtered off, washed twice with 10 ml of methanol and dried at 60° C./125 mmHg for 12 hours, giving 2.0 g (38% of theory) of a greenish-blue solid having a $\lambda_{max}$ (NMP) of 713 nm ($\epsilon$=220 140 $l \cdot mol^{-1} \cdot cm^{-1}$).

EXAMPLE 9

100.0 g (0.41 mol) of 3-(2,4-dimethyl-3-pentoxy) phthalodinitdle, 14.0 g (0,1 mol) of copper(II) chloride, 49.6 g (0.82 mol) of urea and 2.0 g (2% by weight) of ammonium molybdate are introduced into 410 ml of nitrobenzene, and the mixture is heated to 160° C. with stirring under an argon atmosphere and subsequently stirred at this temperature for 5 hours. The mixture is subsequently cooled to RT, diluted with toluene and filtered through a filter aid. The filtrate is evaporated to dryness at 10° C./$10^{-1}$ mmHg. The residue is dissolved in 1 l of toluene and filtered through 600 g of silica gel with toluene as eluent. The filtrate is evaporated, and the residue is stirred in 1.5 l of methanol, filtered, washed with methanol and dried overnight at 60° C./165 mbar, giving 99.5 g (94% of theory) of a greenish-blue solid having a $\lambda_{max}$ (NMP) of 712 nm ($\epsilon$=197 680 $l \cdot mol^{-1} \cdot cm^{-1}$). Thin layer chromatography shows that the isomers I, II and III are present in a ratio of 5:33:62.

EXAMPLE 4

5 g (20.6 mmol) of 3-(2,4-dimethyl-3-pentoxy) phthalodinitdle, 1.79 g (5,15 mmol) of vanadium(III) acetylacetonate, 2.5 g (41.3 mmol) of urea and 100 mg (2% by weight) of ammonium molybdate are introduced into 20 ml of nitrobenzene, and the mixture is heated to 150° C. with stirring under an argon atmosphere and stirred at this temperature for 4 hours. The mixture is subsequently cooled to RT, diluted with toluene and filtered through a filter aid. The filtrate is evaporated to dryness and filtered through 150 g of silica gel with hexanelethyl acetate=25:1. The green fraction is evaporated, taken up in 15 ml of toluene and added dropwise to 300 ml of methanol. The precipitate is filtered off and dried overnight at 60° C./165 mbar, giving 1.9 g (36.1% of theory) of a green solid having a $\lambda_{max}$ (NMP) of 743 nm ($\epsilon$=180 860 $l \cdot mol^{-1} \cdot cm^{-1}$) and a vanadium content of 4.52%.

EXAMPLE 5

15 g (61.9 mmol) of 4-(2,4-dimethyl-3-pentoxy) phthalodinitrile, 2.74 g (15.48 mmol) of palladium(II) chloride, 7.43 g (123.8 mmol) of urea and 300 mg (2% by weight) of ammonium molybdate are introduced into 60 ml of nitrobenzene, and the mixture is heated to 160° C. with stirring under an argon atmosphere and stirred at this temperature for 24 hours. The mixture is then cooled to RT, diluted with toluene and filtered through a filter aid. The filtrate is evaporated to dryness and filtered through 200 g of silica gel with toluene. The blue fraction is evaporated, the residue is taken up in 50 ml of toluene, and the solution is added dropwise to 700 ml of methanol. The precipitate is filtered off and dried overnight at 60° C./165 mbar, giving 8.0 g (48.0% of theory) of a blue solid having a $\lambda_{max}$ (NMP) of 675 nm.

COMPARATIVE EXAMPLE 1

20 g of urea, 5.0 g (20.6 mmol) of 3-(2,4-dimethyl-3-pentoxy)-phthalodinitrile, 0.91 g (5.2 mmol) of anhydrous palladium chloride and 100 mg of ammonium molybdate are heated at 160° C. for 7 hours with stirring under an argon atmosphere. Initially, a brown suspension forms, which solidifies during the course of the reaction. The mixture is subsequently cooled, the solid is taken up in methylene chloride, and the solution is filtered. 80 g of silica gel are then added, and the solvent is evaporated. The loaded silica gel is transferred onto a glass suction filter, and the product is eluted using 1 l of hexane/ethyl acetate 25:1. The eluate is evaporated, the residue is dissolved in 15 ml of toluene and the solution is added dropwise to 300 ml of methanol. The precipitate is filtered off and washed twice with 10 ml of methanol, then dried for 12 hours at 60° C./165 mbar, giving 1.2 g (21.6% of theory) of a blue-green powder having a $\lambda_{max}$ (NMP) of 702 nm ($\epsilon$=195 780 l·mol$^{-1}$·cm$^{-1}$).

COMPARATIVE EXAMPLE 2

5.0 g (20.6 mmol) of 3-(2,4-dimethyl-3-pentoxy) phthalodinitrile, 1.09 g (6.2 mmol) of anhydrous palladium chloride and 100 mg of ammonium molybdate are introduced into 20 ml of nitrobenzene, and the mixture is heated at 160° C. for 4 hours with stirring under an argon atmosphere. The mixture is subsequently cooled and filtered, the solid is washed well with toluene and the filtrate is evaporated to dryness in a high vacuum at 110° C. The crude product is dissolved in methylene chloride, 70 g of silica gel are added, and the solvent is evaporated. The loaded silica gel is transferred onto a glass suction filter, and the product is eluted using hexane/ethyl acetate 25:1. The eluate is evaporated, and the residue is dried for 12 hours at 60° C./165 mbar, giving 0.80 g (14%) of a blue-green powder having a $\lambda_{max}$ (NMP) of 702 nm ($\epsilon$=225 080 l·mol$^{-1}$·cm$^{-1}$).

What is claimed is:

1. A mixture of isomeric α-alkoxy-substituted phthalocyanines of the formulae I–IV

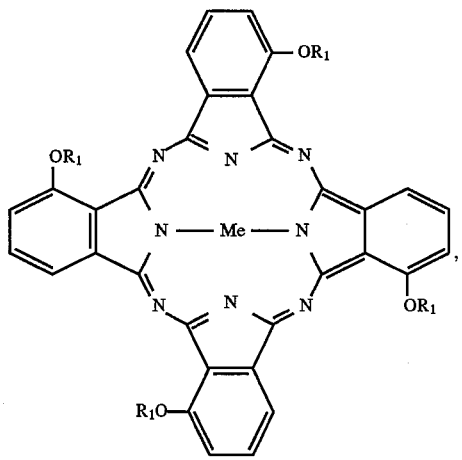
(I)

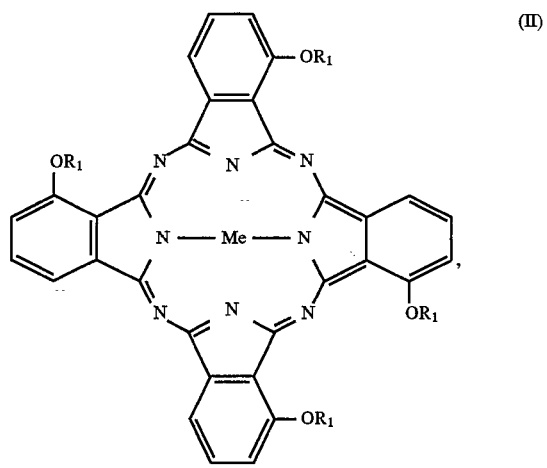
(II)

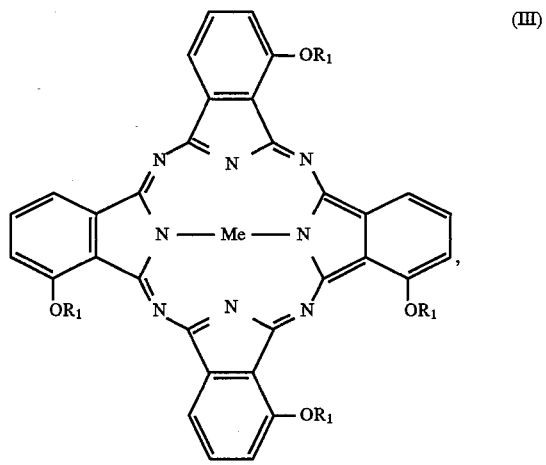
(III)

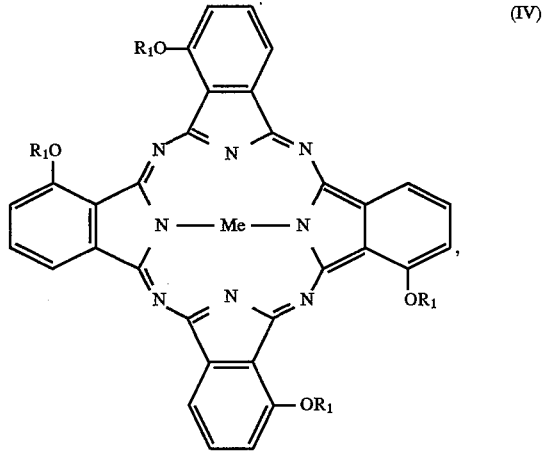
(IV)

or β-alkoxy-substituted phthalocyanines of the formulae Ia–IVa

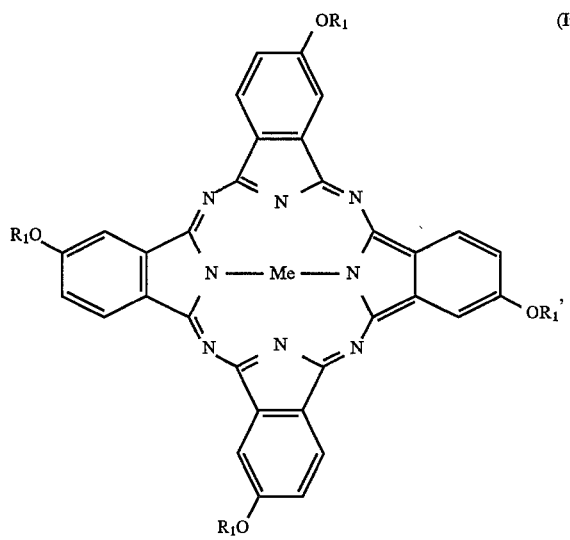
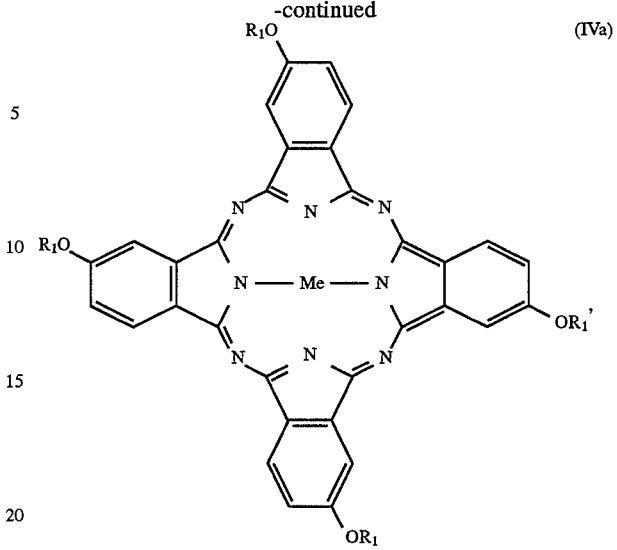

where

Me is a divalent metal atom or a divalent oxo metal, $R_1$ is a linear or branched $C_1$–$C_{16}$alkyl, $C_3$–$C_{16}$alkenyl or $C_3$–$C_{16}$alkynyl radical, which is unsubstituted or substituted by $C_1$–$C_{12}$alkoxy, —CN, $NO_2$, halogen, —OH, phenyl, cyanophenyl, nitrophenyl, halophenyl, hydroxyphenyl or ($C_1$–$C_{12}$alkoxy)phenyl, wherein the isomers of the formula II or IIa and of the formula III or IIIa make up at least 90% of the total mixture, and the isomers of the formula I or Ia and of the formula IV or IVa make up at most 10% of the total mixture, with the ratio between the compounds of the formula II or IIa and the compounds of the formula III or IIIa being from 0.3 to 3.0:1.

2. An isomer mixture according to claim 1, wherein the isomers of the formula II or IIa and of the formula III or IIIa make up at least 95% of the total mixture and the isomers of the formula I or Ia and of the formula IV or IVa make up at most 5% of the total mixture.

3. An isomer mixture according to claim 1, wherein the divalent metal atom or oxo metal Me is Cu(II), Zn(II), Fe(II), Ni(II), Ru(II), Rh(II), Pd(II), Pt(II), Mn(II), Mg(II), Be(II), Ca(II), Ba(II), Cd(II), Hg(II), Sn(II), Co(II), Pb(II) or VO, MnO, TiO.

4. An isomer mixture according to claim 1, wherein the divalent metal atom is Zn(II), Sn(II), Cu(II), Ni(II), Co(II), Pb(II) or Pd(II).

5. An isomer mixture according to claim 1, wherein the divalent metal atom is Cu(II), Ni(II) or Pd(II).

6. An isomer mixture according to claim 1, wherein the divalent metal atom is Cu(II).

7. An isomer mixture according to claim 1, wherein the divalent metal atom is Pd(II).

8. An isomer mixture according to claim 1, wherein $R_1$ is a linear or branched $C_1$–$C_{16}$alkyl radical which is unsubstituted or substituted by $C_1$–$C_{12}$alkoxy, —CN, $NO_2$, halogen, —OH, phenyl, cyanophenyl, nitrophenyl, halophenyl, hydroxyphenyl or ($C_1$–$C_{12}$alkoxy)phenyl.

9. An isomer mixture according to claim 8, wherein $R_1$ is a linear or branched $C_4$–$C_{12}$alkyl radical which is unsubsituted or substituted by $C_1$–$C_{12}$alkoxy, —CN, $NO_2$, halogen, —OH, phenyl, cyanophenyl, nitrophenyl, halophenyl, hydroxyphenyl or ($C_1$–$C_{12}$alkoxy)phenyl.

10. An isomer mixture according to claim 9 wherein $R_1$ is an unsubstituted linear or branched $C_4$–$C_{12}$alkyl radical.

11. An isomer mixture according to claim 1, which comprises the compounds of the formulae I to IV.

12. An isomer mixture according to claim 1, wherein the ratio is from 0.5 to 2.0:1.

* * * * *